US00PP34381P3

(12) United States Plant Patent
Post

(10) Patent No.: US PP34,381 P3
(45) Date of Patent: Jun. 28, 2022

(54) ***CHRYSANTHEMUM* PLANT NAMED 'DLFTAZA4'**

(50) Latin Name: ***Chyrsanthemum* X *morifolium***
Varietal Denomination: DLFTAZA4

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/503,130

(22) Filed: Oct. 15, 2021

(65) Prior Publication Data

US 2022/0124950 P1 Apr. 21, 2022

Related U.S. Application Data

(60) Provisional application No. 63/093,198, filed on Oct. 17, 2020.

(51) Int. Cl.
*A01H 5/02* (2018.01)
*A01H 6/14* (2018.01)

(52) U.S. Cl.
USPC ..... Plt./287

(58) Field of Classification Search
USPC ..... Plt./287, 291
CPC ... A01H 5/02; A01H 5/00; A01H 6/14; A01H 6/1424
See application file for complete search history.

(56) References Cited

PUBLICATIONS

CPVO Register 4.1.23, retrieved on Jan. 13, 2022, retrieved from the Internet at https://online.plantvarieties.eu/publicConsultationDetails?registerId=20201818&denomination=dlftaza4, 3 pp. (Year: 2022).*

* cited by examiner

*Primary Examiner* — June Hwu
(74) *Attorney, Agent, or Firm* — C. Anne Whealy

(57) ABSTRACT

A new and distinct cultivar of *Chrysanthemum* plant named 'DLFTAZA4', characterized by its upright plant habit; uniform growth habit; dark green-colored leaves; uniform flowering habit; strong upright flowering stems; large and dense decorative-type inflorescences with quilled ray florets that are purplish red in color with greenish yellow-colored apices; resistance to *Fusarium*; and good postproduction longevity.

1 Drawing Sheet

Figure 1:
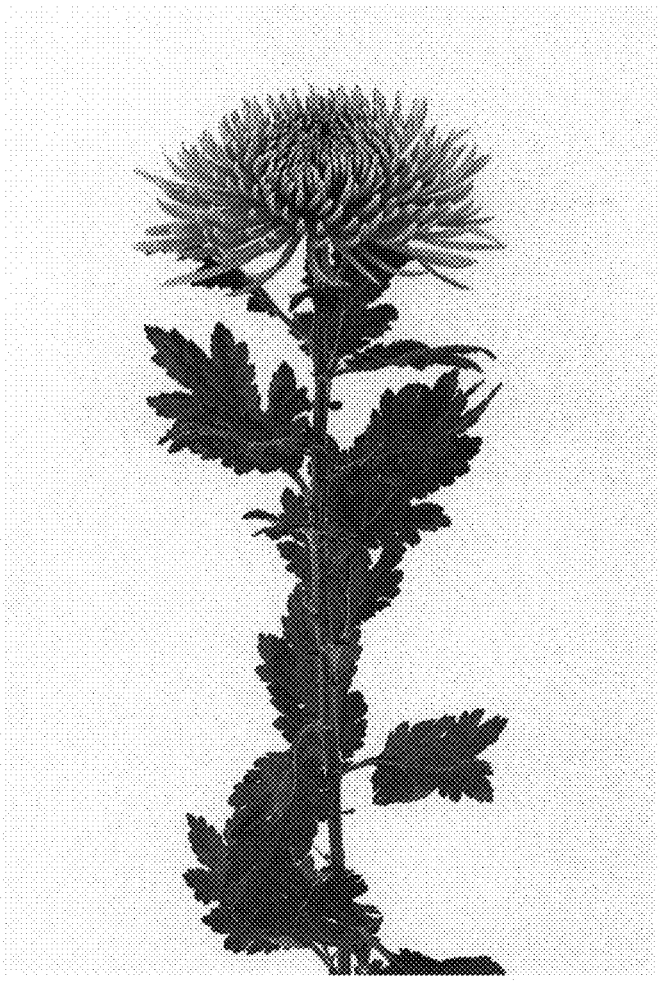

Botanical designation: *Chrysanthemum* X *morifolium*.
Cultivar denomination: 'DLFTAZA4'.

STATEMENT REGARDING PRIOR DISCLOSURES BY INVENTOR/APPLICANT & ASSIGNEE

An European Plant Breeders' Rights application for the instant plant was filed by the Assignee, Deliflor Royalties B.V. of Maasdijk, The Netherlands on Jul. 30, 2020, application number 2020/1818. Foreign priority is not claimed to this application.

A Japanese Plant Breeders' Rights application for the instant plant was filed by the Assignee, Deliflor Royalties B.V. of Maasdijk, The Netherlands on Aug. 31, 2020, application number 34906. Foreign priority is not claimed to this application.

A Taiwanese Plant Breeders' Rights application for the instant plant was filed by the Assignee, Deliflor Royalties B.V. of Maasdijk, The Netherlands on Dec. 25, 2020, application number 1090171. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFTAZA4'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'DLFTAZA10', not patented. The new *Chrysanthemum* plant was discovered and selected as a single flowering plant from within a population of plants of 'DLFTAZA10' in a controlled greenhouse environment in Maasdijk, The Netherlands in June, 2018.

Asexual reproduction of the new *Chrysanthemum* plant by vegetative terminal cuttings since June, 2018 in a controlled greenhouse environment in Maasdijk, The Netherlands, has shown that the unique features of this new

*Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFTAZA4'. These characteristics in combination distinguish 'DLFTAZA4' as a new and distinct *Chrysanthemum* plant:

1. Upright plant habit; uniform growth habit.
2. Dark green-colored leaves.
3. Uniform flowering habit.
4. Strong upright flowering stems.
5. Large and dense decorative-type inflorescences with quilled ray florets that are purplish red in color with greenish yellow-colored apices.
6. Resistant to *Fusarium* (*Fusarium oxysporum*).
7. Good postproduction longevity.

Plants of the new *Chrysanthemum* differ primarily from plants of the mutation parent, 'DLFTAZA10', in ray floret color as ray florets of plants of the new *Chrysanthemum* are purplish red in color with greenish yellow-colored apices whereas ray florets of plants of 'DLFTAZA10' are white in color with red purple-colored apices.

Plants of the new *Chrysanthemum* can also be compared to plants of *Chrysanthemum* X *morifolium* 'Deliarsenal', not patented. In side-by-side comparisons, plants of the new *Chrysanthemum* differ primarily from plants of 'Deliarsenal' in the following characteristics:

1. Plants of the new *Chrysanthemum* have tubular quilled ray florets whereas plants of 'Deliarsenal' have flattened quilled ray florets.
2. Ray florets of plants of the new *Chrysanthemum* are purplish red in color with greenish yellow-colored apices whereas ray florets of plants of 'Deliarsenal' are purple in color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFTAZA4' grown as a disbud-type cut flower.

Figure 2:
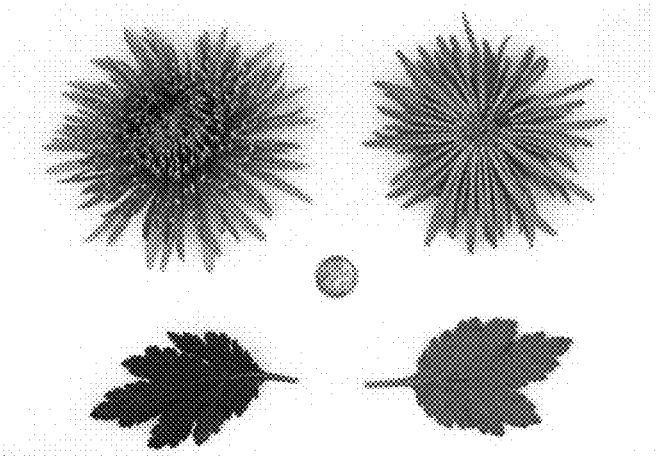

The photograph at the bottom of the sheet (FIG. 2) is a close-up view of upper (left) and lower (right) surfaces of typical inflorescences (top of figure) and typical leaves (bottom of figure) of 'DLFTAZA4'.

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem disbud-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFTAZA4'.

Parentage: Naturally-occurring whole plant mutation of *Chrysanthemum* x *morifolium* 'DLFTAZA10', not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and rapid growth rate.

*Plant height, soil level to top of foliar plane*.—About 64.9 cm.

*Plant height, soil level to top of inflorescence plane*.—About 69.9 cm.

*Plant diameter*.—About 19 cm.

*Flowering stem length*.—About 62.5 cm.

*Flowering stem diameter*.—About 7 mm.

*Flowering stem internode length*.—About 2.6 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 138A.

*Flowering stem color, developed*.—Close to 146A and 148A.

*Leaf description*.—Arrangement: Alternate; simple. Length: About 9.9 cm. Width: About 6.4 cm. Shape, in overall outline: Obovate to oblong. Apex: Abruptly acute, minute. Base: Attenuate. Margin: Palmately lobed, coarsely crenate to dentate to serrate to dentate; sinuses convergent to divergent and shallow to medium in depth. Texture and luster, upper surface: Moderately pubescent, not rugose; moderately velvety; slightly glossy. Texture and luster, lower surface: Densely pubescent, prominent venation; slightly velvety; slightly glossy. Venation pattern: Pinnate, reticulate. Color: Developing leaves, upper surface: Close to 137A. Developing leaves, lower surface: Close to between 138A and 147B. Fully developed leaves, upper surface:

Slightly darker than 147A; venation, close to 146B to 146C. Fully developed leaves, lower surface: Close to 147B; venation, close to 146C. Petioles: Length: About 1.8 cm. Diameter: About 3 mm by 4 mm. Strength: Moderately strong. Texture and luster, upper surface: Densely pubescent; slightly glossy. Texture and luster, lower surface: Densely pubescent; moderately glossy. Color, upper surface: Close to 146B; edges, close to NN137A to NN137B. Color, lower surface: Close to 14B; edges, close to 147B. Stipules: Quantity, appearance and arrangement: Two leafy stipules, opposite, at the petiole attachment to the stem. Length: About 1 cm. Width: About 1.2 cm. Shape, in overall outline: Roughly reniform with emarginate apices. Texture and luster, upper surface: Moderately pubescent; slightly glossy. Texture and luster, lower surface: Densely pubescent; slightly glossy. Color, upper surface: Slightly darker than 147A. Color, lower surface: Close to 147B.

Inflorescence description:

*Appearance*.—Large and dense decorative-type inflorescence form with quilled-shaped ray florets and tubular disc florets; inflorescences borne perpendicular to peduncles and face mostly upright; ray and disc florets develop acropetally on a capitulum; typically grown as a disbud-type, but can also be grown as a spray-type.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 56 days later when grown as a disbud-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a disbud-type, however, when grown as a spray-type, about 31 inflorescences develop per flowering stem.

*Inflorescence size*.—Diameter, grown as a disbud-type: About 15.6 cm. Depth (height), grown as a disbud-type: About 6.8 cm. Disc diameter, grown as a disbud-type: About 2 mm to 4 mm; inconspicuous. Diameter, grown as a spray-type: About 10.1 cm. Depth (height), grown as a spray-type: About 3 cm. Disc diameter, grown as a spray-type: About 2 mm to 4 mm; inconspicuous.

*Receptacles*.—Height, grown as a disbud-type: About 2.1 cm. Diameter, grown as a disbud-type: About 8 mm. Height, grown as a spray-type: About 1 cm. Diameter, grown as a spray-type: About 5 mm. Shape: Flattened globular. Color: Close to 145B and 146A.

*Inflorescence buds*.—Height: About 1.2 cm. Diameter: About 1.4 cm. Shape: Flattened spherical. Texture and luster: Distally, smooth and glabrous; proximally, moderately pubescent; slightly glossy. Color: Developing involucral bracts, close to 137A and 138C to 138D; developing ray florets, close to 1C slightly tinged with close to 37B.

*Ray florets*.—Quantity and arrangement: About 2,000 arranged in about 22 whorls. Length, when grown as a disbud-type: About 5.1 cm; varying between 0.5 cm and 8.7 cm. Width, when grown as a disbud-type: About 4 mm; varying between 1 mm and 7 mm. Length, when grown as a spray-type: About 2.9 cm; varying between 0.4 cm and 5 cm. Width, when grown as a spray-type: About 2.5 mm; varying between 1 mm and 4.5 mm. Shape: Quilled; apices incurved. Apex: Shallowly praemorse. Base: Fused. Aspect: About 35° from vertical. Texture and luster, inner surface: Smooth, glabrous; slightly velvety; matte. Texture and luster, outer surface: Smooth, glabrous; slightly glossy. Color: When opening, inner surface: Close to 1C and towards the apices, close to 145D; with development, color becoming closer to 11C. When opening, outer surface: Close to 164C and towards the base, close to 153D; with development, color becoming closer to 176A and towards the base, close to 151C to 151D. Fully opened, inner surface: Close to 11D densely covered with fine dots, close to 185C and 185D; towards the apex, close to 145D and towards the base, close to 1C; venation, similar to lamina colors; colors do not change with subsequent development. Fully opened, outer surface: Close to 181C and 184C; towards the apex, close to 151C; with development, color becoming closer to 184D and 185C and towards the apex, close to 151B; venation, similar to lamina colors; colors do not change with subsequent development.

*Disc florets*.—Quantity and arrangement: About 5 to 20 massed randomly at the center of the receptacle. Length: About 5 mm. Diameter: About 1 mm. Shape: Lower 80% fused into a tube; upper 20% free. Apex: Acute. Margin, free-part: Entire. Texture and luster, inner and outer surfaces: Smooth, glabrous; glossy. Color, when opening, inner and outer surfaces: Apex: Close to N144A. Mid-section: Close to 11C. Base: Close to 145C. Color, fully opened, inner and outer surfaces: Apex: Close to N144A. Mid-section: Close to 11C. Base: Close to 145C.

*Involucral bracts*.—Quantity and arrangement: About 44 arranged in about two whorls. Length: About 1.3 cm. Width: About 3.5 mm. Shape: Narrowly ovate. Apex: Narrowly obtuse. Base: Cuneate. Margin: Entire. Texture and luster, upper surface: Smooth, glabrous; glossy. Texture and luster, lower surface: Moderately pubescent; matte. Color, upper surface: Close to 138A; towards the apex, close to NN137A; lateral margins, translucent and close to 157C to 157D and apical margins tinged with close to N199A. Color, lower surface: Close to NN137A; lateral margins, translucent and close to 157C to 157D and apical margins tinged with close to N199A.

*Peduncles*.—Length, terminal peduncle: About 4.1 cm. Diameter, terminal peduncle: About 6 mm. Length, third peduncle: About 6.7 cm. Diameter, third peduncle: About 3.5 mm. Strength: Strong. Aspect, terminal peduncle: Upright. Aspect, third peduncle:

About 45° from the flowering stem axis. Texture and luster: Densely pubescent; moderately glossy. Color: Close to 143A and N148D.

*Reproductive organs*.—Androecium: Present on disc florets only. Quantity: About five per floret. Filament length: About 2 mm. Filament color: Close to 145D. Anther size: About 0.5 mm by 2 mm. Anther shape: Oblong. Anther color: Close to 13A. Pollen amount: None observed. Gynoecium: Present on both ray and disc florets. Quantity: One per floret. Pistil length: About 8.5 mm. Style length: About 7 mm. Style color: Close to N144B. Stigma diameter: About 3 mm. Stigma shape: Cleft to three-parted, decurrent. Stigma color: Close to 12B. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* (*Fusarium oxysporum*). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFTAZA4' as illustrated and described.

* * * * *